US00PP23016P3

(12) United States Plant Patent
Blom

(10) Patent No.: US PP23,016 P3
(45) Date of Patent: Sep. 4, 2012

(54) ***CHRYSANTHEMUM* PLANT NAMED 'ZANMUROVER'**

(50) Latin Name: ***Chrysanthemum×morifolium* Ramat.**
Varietal Denomination: Zanmurover

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 13 days.

(21) Appl. No.: 12/926,550

(22) Filed: Nov. 24, 2010

(65) Prior Publication Data
US 2012/0131713 P1 May 24, 2012

(51) Int. Cl.
*A01H 5/00* (2006.01)

(52) U.S. Cl. ..... Plt./298

(58) Field of Classification Search ..... Plt./298
See application file for complete search history.

*Primary Examiner* — Susan McCormick Ewoldt
(74) *Attorney, Agent, or Firm* — Steptoe & Johnson LLP

(57) ABSTRACT

A *chrysanthemum* plant named 'Zanmurover' characterized by its medium sized blooms with dark red ray florets and prolific branching; natural season flower date October 5 (week 41); blooming for a period of 4 weeks.

3 Drawing Sheets

Botanical designation: *Chrysanthemum×morifolium* Ramat.

Cultivar denomination: 'Zanmurover'.

RELATED CULTIVARS

This new plant cultivar 'Zanmurover' is of the botanical classification *Chrysanthemum×morifolium* Ramat, and is related to 'Zanmucanyon' (U.S. Plant patent application Ser. No. 12/926,546). Both cultivars have been obtained as seedlings from the same cross.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmurover'. 'Zanmurover' is a product of a breeding and selection program for outdoor pot mums (garden mums) which had the objective of creating new cultivars with a double type inflorescence, a natural season flower date around October 5 (week 41), blooming for a period of 4 weeks. 'Zanmurover' is a seedling resulting from a cross of the female parent id 9396 with the male parent id 9285. Plants of the new cultivar 'Zanmurover' differ from plants of the female parent in the following characteristics. (1) Natural season flowering date. And (2) Inflorescence size. (1). Plants of the seedling flower later in the season than those of the female parent. (2) Inflorescences of the seedling are smaller than those of the female parent. Plants of the new cultivar 'Zanmurover' differ from plants of the male parent in the presence of disc florets. Disc florets are absent in the seedling, while they are present in the mature inflorescences of the male parent.

The new and distinct cultivar was discovered and selected as a flowering plant by Wilhelmus Bernardus Blom on a cultivated field in Rijsenhout, The Netherlands in 2005. The first act of asexual production of 'Zanmurover' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
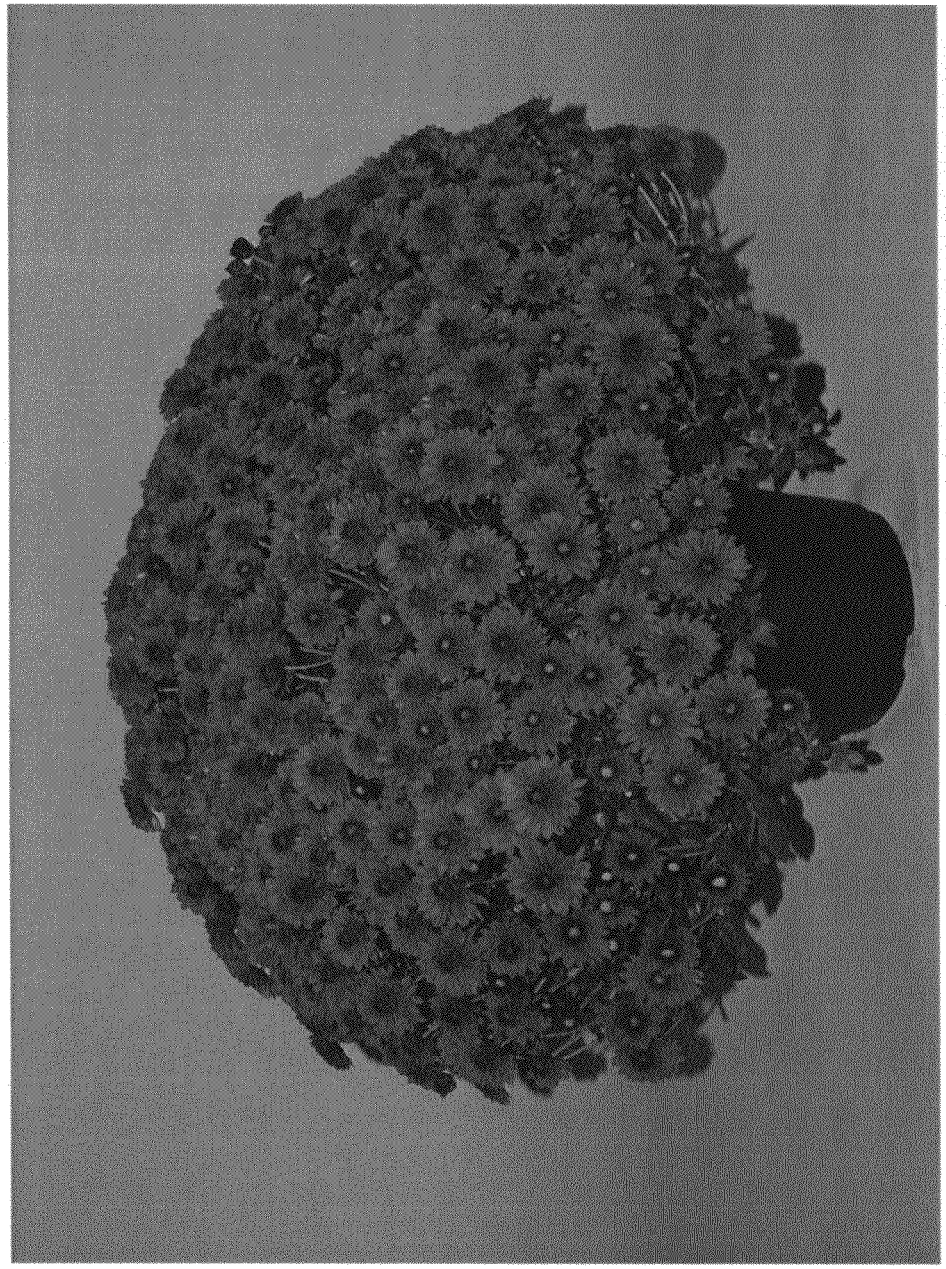
FIG. 1 shows a plant of the cultivar in full bloom.
Figure 2:
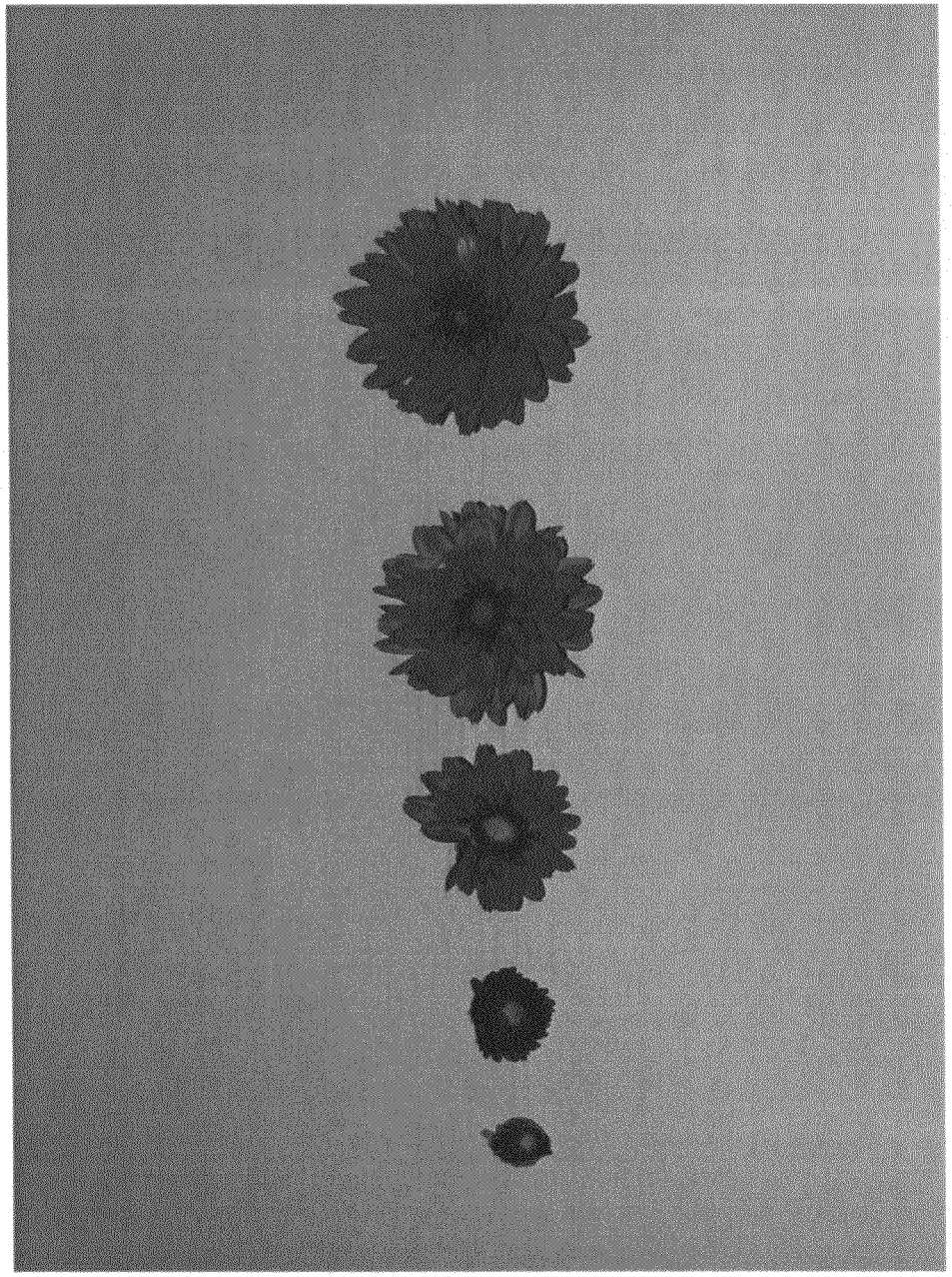
FIG. 2 shows the various stages of bloom of the new cultivar.
Figure 3:
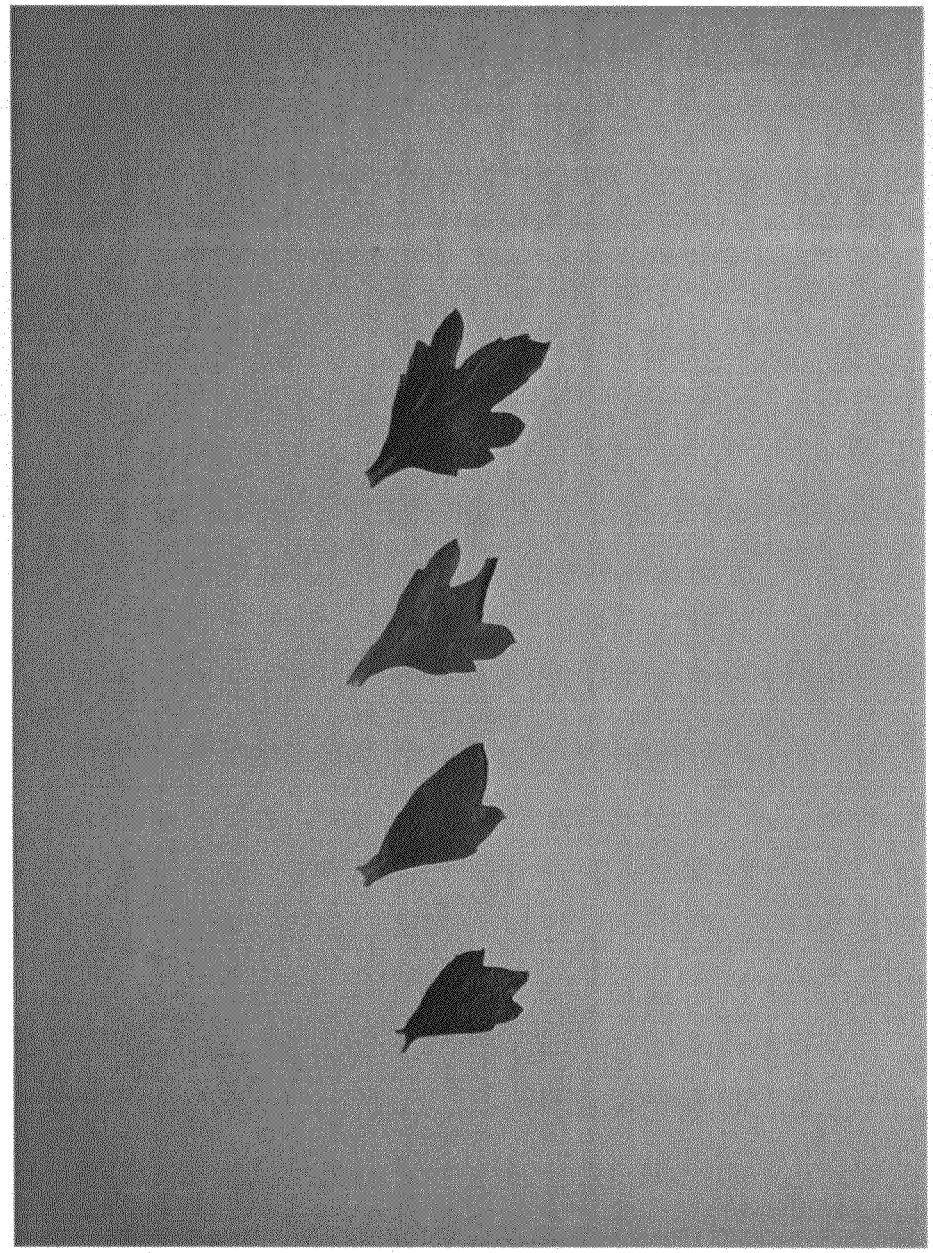
FIG. 3 shows the various stages of foliage of the new cultivar.

The observations and measurements were gathered from plants grown out door in Rijsenhout, The Netherlands under natural day length and temperature and planted in week 23 in 2009. The natural season flowering date of this crop was October 5 (week 41) . The average height of the plants was 30 cm. No growth retardants were used. No tests were done on disease or insect resistance or susceptibility. No tests were done on cold or drought tolerance. This new variety produces medium sized blooms with dark red ray florets blooming for a period of 4 weeks.

From the cultivars known to inventor the most similar existing cultivar in comparison to 'Zanmurover' is its sibling 'Zanmucanyon' (U.S. Plant Pat. No. 22,620). When 'Zanmucanyon' and 'Zanmurover' are being compared the following differences are noticed:(1) Plant vigor. And (2) Leaf size. (1) Plants of 'Zanmurover' are more vigorous than those of 'Zanmucanyon'. (2) Leaves of 'Zanmurover' are smaller than those of 'Zanmucanyon'.

The following is a description of the plant and characteristics that distinguish 'Zanmurover' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmuroner'

| | |
|---|---|
| Bud | |
| Size | Small; cross-section 5 mm, height 5 mm |
| Shape | Round |
| Texture | Pubescent |
| Outside Color | Greyed-green 191A |
| Phyllaries | |
| Number | 25, arranged in 3 rows |
| Shape | Elliptic |
| Apex | Acute |
| Base | Truncate |
| Margin | Entire |
| Color | Upper surface: Greyed-green 191B |
| Length and width | 5 mm; 2 mm |
| Texture | Pubescent |
| Inflorescence | |
| Type | Double |
| Height | 1 cm |
| Diameter | 4 cm |
| Peduncle length | 6 cm |
| Peduncle color | Green 138B |
| Peduncle diameter | 1.8 mm |
| Peduncle texture | Pubescent |
| Number per branch | Approx 7 inflorescences |
| Duration of flowering | 4 weeks |
| Seeds | Produced in small quantities, ovate, Greyed-brown 199A, length 1.5 mm, diameter 0.5 mm |
| Color | |
| Center of inflorescence | Immature stage: Greyed-red 181A<br>Mature stage: Greyed-yellow 161D |
| Color of upper surface of the ray-florets | Yellow 6C at base, Greyed-red 181B at top |
| Color of the lower surface of the ray-florets | Greyed-red 180D |
| Tonality from Distance | A garden mum with dark red flowers |
| Color of the ray-florets after aging of the plant | Greyed-red 180C |
| Ray florets | |
| Texture | Upper and lower surface smooth |
| Number | Ca 180 |
| Shape | Elliptic |
| Apex | Dentate |
| Base | Attenuate |
| Cross-section | Flat |
| Longitudinal axis of majority | Straight |
| Length of corolla tube | 3-4 mm |
| Ray-floret margin | Entire |
| Ray-floret length | 1.1-1.6 cm |
| Ray-floret width | 4 mm |
| Ratio length/width | Medium |
| Disc florets | Absent |
| Receptacle | |
| Color | Yellow-green 145D |
| Shape | Conical raised |
| Height | 5 mm |
| Diameter | 2 mm |

TABLE 1-continued

Botanical Description of *Chrysanthemum xmorifolium* Ramat. 'Zanmuroner'

| | |
|---|---|
| Reproductive Organs | |
| Androecium | Absent |
| Pollen | Not produced |
| Gynoecium | Present on ray florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Grown as a spray type pot mum, outdoor raised and mounded |
| Growth habit | Spherical shape |
| Growth rate | High |
| Height | 30 cm |
| Width | 50 cm |
| Stem Color | Greyed-brown 199A |
| Stem Strength | Strong |
| Stem Brittleness | Brittle |
| Stem Anthocyanin Coloration | Not observed |
| Internode length | 1-2 cm |
| Length of lateral branch | From top to bottom 15 cm |
| Lateral branch color | Green 137 C |
| Lateral branch, attachment | Weak |
| Lateral branch diameter | 2. mm |
| Branching (average number of lateral branches) | Prolific with 8 breaks after pinching |
| Natural season blooming date | October 5 (week 41) |
| Foliage | |
| Leaf color | Upper side: Yellow-green 147B<br>Lower side: Yellow-green 147C |
| Color midvein | Upper side: Yellow-green 147D<br>Lower side: Yellow-green 148D |
| Size | Small; length 2.5-4 cm, width 1.5-2.5 cm |
| Quantity (number per lateral branch) | 16-18 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate |
| Apex | Mucronulate |
| Petiole length | 0.5-1 cm |
| Petiole diameter | 2 mm |
| Petiole color | Yellow-green 147D |

TABLE 2

Differences with the comparison variety (when grown side to side)

| | "Zanmurover" | 'Zanmucanyon' |
|---|---|---|
| Growth rate | High | Medium |
| Leaf length | 2.5-4 cm | 4-5 cm |
| Leaf width | 1.5-2.5 cm | 3-3.5 cm |

I claim:

1. A new and distinct *chrysanthemum* plant named 'Zanmurover' as described and illustrated.

* * * * *